(12) United States Patent
Hentz et al.

(10) Patent No.: US 9,506,852 B2
(45) Date of Patent: Nov. 29, 2016

(54) DEVICE FOR DETERMINING THE MASS OF A PARTICLE IN SUSPENSION OR IN SOLUTION IN A FLUID

(71) Applicant: COMMISSARIAT A L'ENERGIE ATOMIQUE ET AUX ENE ALT, Paris (FR)

(72) Inventors: Sebastien Hentz, Varces Allieres et Risset (FR); Christophe Masselon, Corenc (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 130 days.

(21) Appl. No.: 14/202,490

(22) Filed: Mar. 10, 2014

(65) Prior Publication Data

US 2014/0250980 A1    Sep. 11, 2014

(30) Foreign Application Priority Data

Mar. 11, 2013    (FR) .................................... 13 52154

(51) Int. Cl.
*G01N 7/00* (2006.01)
*G01N 9/00* (2006.01)
*G01N 19/10* (2006.01)
*G01N 25/00* (2006.01)
*G01N 27/00* (2006.01)
*G01N 29/02* (2006.01)
*G01N 33/497* (2006.01)
*G01N 15/10* (2006.01)
*G01G 3/16* (2006.01)

(52) U.S. Cl.
CPC ................ *G01N 15/10* (2013.01); *G01G 3/16* (2013.01); *G01N 29/022* (2013.01)

(58) Field of Classification Search
None
See application file for complete search history.

(56) References Cited

U.S. PATENT DOCUMENTS

| 6,722,200 | B2 | 4/2004 | Roukes et al. |
| 6,906,322 | B2 * | 6/2005 | Berggren ............... H01J 49/165 250/281 |
| 6,972,408 | B1 * | 12/2005 | Reilly ..................... H01J 49/04 250/251 |
| 7,479,630 | B2 * | 1/2009 | Bandura ............ G01N 15/1404 250/281 |

(Continued)

FOREIGN PATENT DOCUMENTS

FR    2 979 705 A1    3/2013
WO    WO 2011/060369 A1    5/2011

(Continued)

OTHER PUBLICATIONS

K. L. Ekinci, et al., "Ultrasensitive nanoelectromechanical mass detection" Applied Physics Letters, vol. 84, No. 22, May 31, 2004, pp. 4469-4471.

(Continued)

*Primary Examiner* — Andre Allen
*Assistant Examiner* — Jermaine Jenkins
(74) *Attorney, Agent, or Firm* — Oblon, McClelland, Maier & Neustadt, L.L.P.

(57) ABSTRACT

A device is provided for determining the mass of a particle in suspension or in solution in a fluid, including a first device for the nebulization of the fluid to obtain a flux comprising at least the particle; a second device for the guidance and the aerodynamic focusing of the flux; and a third device for determining the mass of the particle by a frequency measurement, the third device including at least one gravimetric detector, arranged opposite an outlet of the second device, to receive the particle.

11 Claims, 2 Drawing Sheets

(56) References Cited

U.S. PATENT DOCUMENTS

| | | | |
|---|---|---|---|
| 7,642,511 B2* | 1/2010 | Reilly | H01J 49/067 250/251 |
| 8,539,840 B2* | 9/2013 | Ariessohn | B08B 3/12 73/860 |
| 8,963,076 B2* | 2/2015 | Jong | G01N 35/10 250/281 |
| 2008/0022853 A1 | 1/2008 | Ariessohn | |
| 2011/0186167 A1 | 8/2011 | Lee et al. | |
| 2012/0199736 A1 | 8/2012 | Danel et al. | |
| 2013/0154440 A1 | 6/2013 | Hentz | |
| 2013/0160550 A1 | 6/2013 | Hentz | |
| 2013/0214644 A1 | 8/2013 | Hentz et al. | |
| 2015/0231340 A1* | 8/2015 | Pumphrey | A61M 11/005 128/200.16 |

FOREIGN PATENT DOCUMENTS

| | | |
|---|---|---|
| WO | WO 2012/034949 A1 | 3/2012 |
| WO | WO 2012/034951 A1 | 3/2012 |
| WO | WO 2012/034990 A1 | 3/2012 |

OTHER PUBLICATIONS

S. Dohn, et al., "Mass and position determination of attached particles on cantilever based mass sensors" Review of Scientific Instruments, vol. 78, No. 103303, 2007, 3 Pages.

Jonghoo Park, et al., "A Mechanical Nanomembrane Detector for Time-of-Flight Mass Spectrometry" Nano Letters, vol. 11, 2011, pp. 3681-3684.

"ARI Aerosol Mass Spectrometer", Operation Manual, Aerodyne Research, Inc. Nov. 17, 2005, 23 Pages.

French Preliminary Search Report issued Nov. 7, 2013, in Patent Application No. FR 1352154, filed Mar. 11, 2013 (with English Translation of Category of Cited Documents).

A. K. Naik, et al., "Towards single-molecule nanomechanical mass spectrometry", Nature Nanotechnology, vol. 4, No. 7, XP 055024639, Jun. 21, 2009, pp. 445-450.

* cited by examiner

DEVICE FOR DETERMINING THE MASS OF A PARTICLE IN SUSPENSION OR IN SOLUTION IN A FLUID

TECHNICAL FIELD

The present invention relates to a device for determining the mass of a particle in suspension or in solution in a fluid.

It applies in particular to mass spectrometry for species which are neutral or ionized.

STATE OF THE PRIOR ART

Conventional mass spectrometry (MS) is a universal chemical or biological analytical tool that is based on four essential components: an injection system, an ionization source, a mass analyser and an ion detector. These components are arranged in an enclosure, provided with pumps to create a vacuum therein.

The result of a mass spectrometry measurement is a spectrum that reflects the abundance, in a mixture, of a type of species as a function of the mass/charge ratio of said species. Each peak of the spectrum is the signature of a mono-charged or multi-charged ion; and the identification of species is achieved by means of a pre-established data bank.

The technique that has been described has now become a standard for numerous applications. However, it has a certain number of drawbacks:

- this technique is relatively long to implement and it is not very sensitive: a lot of biological material is necessary to perform a measurement;
- commercially available mass spectrometry devices are all extremely bulky: they occupy a volume of the order of a few cubic metres; and they are expensive: they cost several hundreds of thousands of euros; and
- this technique does not make it possible to measure important masses which are typically above 100 kDa ($1.66 \times 10^{-22}$ kg), masses for which the measurement resolution becomes completely insufficient.

This latter drawback results mainly from the difficulty of accelerating sufficiently a heavy particle, and thus to give it sufficient energy so that it can reach the ion detector. It is however vital to be able to measure particles whose masses are greater than 100 kDa ($1.66 \times 10^{-22}$ kg), since they can have fundamental importance in the biomedical field: they may be for example viruses, bacteria, organelles, protein complexes or cells.

Another technique has been proposed for detecting masses using NEMS, in other words nano-electro-mechanical systems. And NEMS based resonant devices have been elaborated for which the detection limits are $10^{12}$ times lower than those of QCM, in other words quartz crystal microbalances, which are commercially available. In this respect, reference may be made to the following documents:

K. L. Ekinci, X. M. H. Huang and M. L. Roukes, 2004, "Ultrasensitive nanoelectromechanical mass detection", *Applied Physics Letters* 84 (22): 4469. doi: 10.1063/1.1755417

Michael L. Roukes and Kamil L. Ekinci, 2004, "Apparatus and method for ultrasensitive nanoelectromechanical mass detection", U.S. Pat. No. 6,722,200

The principle of such a NEMS based resonating device is explained hereafter.

A particle of mass $m_p$ settles on the NEMS, of stiffness k and of effective mass m, which increases its total mass. The new resonance frequency of the device is then equal to:

$$f = \frac{1}{2\pi}\sqrt{\frac{k}{m+m_p}}.$$

The frequency response peaks (in open loop), before and after deposition of the mass $m_p$, are thus shifted by a quantity $\Delta f$, which is little different to $$-\frac{m_p}{2m} \cdot \frac{1}{2\pi}\sqrt{\frac{k}{m}}.$$

When the device is used in closed loop, its resonance frequency can thus be monitored in real time using electrical transduction means and loop closure means.

Thus, during its adsorption on a resonating NEMS, an individual particle of analyte, or a group of such particles, makes the resonance frequency of the NEMS drop sharply. And the mass of the particle, or the group of particles, may be deduced from the measurement of the frequency jump $\Delta f$.

Said frequency jump $\Delta f$ depends on the mass of the particle, or the group of particles (see the value of $\Delta f$ given above). But it also depends on the position at which the particle or the group of particles has settled on the surface of the NEMS. When it is not possible—and this is the most common case—to precisely locate the adsorption position of the particles on the NEMS, the frequency jump information alone is not sufficient. Recourse may then be made to a statistical approach, which consists:

in measuring a large number of events, each event corresponding to the arrival of a single particle or a set of particles, said arrival being associated with a frequency jump, and in assuming an equiprobability of position on the surface of the NEMS.

In this respect, reference may be made to the following document:

A. K. Naik, M. S. Hanay, W. K. Hiebert, X. L. Feng and M. L. Roukes, 2009, "Towards single-molecule nanomechanical mass spectrometry", *Nature Nanotechnology* 4: 445-450. doi:10.1038/NNANO.2009.152.

Another solution consists in measuring in real time the frequencies of two modes, or more, of the same NEMS. Several items of information are thereby available. In this respect, reference may be made to the following document:

S. Dohn, W. Svendsen, A. Boisen and O. Hansen, 2007, "Mass and position determination of attached particles on cantilever based mass sensors", *Review of Scientific Instruments* 78: 103303. doi:10.1063/1.2804074.

This mass measurement by means of NEMS has led to using them for performing mass spectrometry, which is then known as N EMS-MS. In this technique, the distribution of the masses of all the particles that are present in a mixture is measured and, to do so, they are sent one after the other onto the surface of a NEMS. This enables biological mass spectrometry, at the level of the individual particle, and procures the following advantages:

due to the integrability of NEMS which can be manufactured in large quantities and in a collective manner on semiconductor wafers, NEMS-MS is a technique that is highly parallelisable, which makes the measurement very quick; and, it becomes possible to envisage manufacturing portable and inexpensive NEMS-MS devices;

the detection of mass using NEMS, which are gravimetric, is sensitive both to ions and to neutral particles; the measurement efficiency is thereby improved by several orders of magnitude; and gravimetric detection provides a mass resolution that is constant over the whole measurement range, and thus provides an excellent resolving power in high masses, unlike conventional techniques.

FIG. 1 of the article of A. K. Naik et al., already cited, shows a known NEMS-MS system, the architecture of which is similar to those of conventional mass spectrometers: biological particles in liquid phase are injected and they are transmitted as efficiently as possible to a NEMS under vacuum, more precisely at a pressure of the order of $10^{-5}$ mTorr ($10^{-6}$ Pa).

To do so, commercially available components are used: the injection source uses an ESI, in other words electrospray ionization, which nebulizes and ionizes the species to be analysed. The latter pass through several differential pumping and ionic guidance stages (using hexapoles), to finally arrive in the NEMS zone.

Such a known system has various drawbacks which do not enable the optimal use of all of the advantages brought by the NEMS-MS technique:

- in this known system, the injection source and the NEMS are very far apart from each other in order to enable differential pumping; considerable losses of species between the source and the NEMS ensue;
- this distance apart imposes guiding the species to the NEMS; and in this system, only ionized species are guided; neutral particles are lost in the system; and
- with such a distance apart, it is very difficult to focus a beam of ions on a surface area less than a few square millimetres; thus, a very low proportion of particles actually settles on the NEMS, the surface area of which is typically of the order of a few square micrometres.

All of these drawbacks make this known system very inefficient and do not make it possible to fully benefit from the advantages of NEMS-MS. In particular, the potential advantage that there would be in using a system dedicated to neutral and/or equally well ionized species may be seen. In fact, transmission by ion optics (and thus by means of electromagnetic fields) of generally heavy species, of the kind of those that are particularly targeted by NEMS-MS (organelles, viruses, bacteria, protein complexes, etc.), is very difficult. To transmit these massive particles with correct efficiency, it would be necessary to render them highly charged, which would have the effect of denaturing them and would no longer make it possible to measure them in their native state.

Resonating devices using NEMS are also known through the following documents:

WO 2012/034949, invention of S. Hentz

WO 2012/034951, invention of S. Hentz et al.

WO 2012/034990, invention of S. Hentz.

DESCRIPTION OF THE INVENTION

The aim of the present invention is to overcome the drawbacks of the known NEMS-MS system, described above, by associating a device for injecting neutral and/or ionized species, a guidance device, and a NEMS type detector, the whole favouring the proximity of these various components.

In a precise manner, the subject matter of the present invention is a device for determining the mass of at least one particle in suspension or in solution in a fluid, characterised in that it comprises:

- a first device for the nebulization of the fluid, to obtain a flux comprising at least said at least one particle,
- a second device for the guidance and the aerodynamic focusing of the flux, said second device comprising an inlet to receive the flux, and an outlet, and
- a third device for determining the mass of said at least one particle by a frequency measurement, said third device comprising at least one gravimetric detector, arranged opposite the outlet of the second device, to receive said at least one particle.

The device, the subject matter of the invention, thus makes it possible to determine the mass of each particle, in suspension or in solution, or a set of particles, depending on the flow rate of the flux used and the type of analyte containing the particles to be analysed. Obviously, "particle" is taken to mean an individual particle or an aggregate of particles.

According to a particular embodiment of the device, the subject matter of the invention, the second device is electrically neutral.

Such an electrically neutral device has the advantage of transmitting equally well positive ions and negative ions as well as neutral particles.

The second device may comprise an aerodynamic lens.

Said aerodynamic lens may be associated, at the outlet, with an orifice.

Preferably, the device, the subject matter of the invention, further comprises:

- a zone at a given pressure, containing the first device, and
- at least one vacuum enclosure, or first enclosure, provided to be at a first pressure, below the pressure of said zone, the first enclosure communicating with the zone and containing at least one part of the second device.

"Given pressure" is taken to mean a pressure that may be an air pressure (atmospheric pressure) or a pressure of another gas, depending on the envisaged application for the invention.

Then, the second device may further comprise a capillary having an inlet orifice in the zone and an output orifice in the first enclosure, to place the zone in communication with the first enclosure.

In this case, the second device may comprise an aerodynamic lens opposite the inlet and/or outlet orifice of the capillary.

Thus, the concentration or focusing of the flux can take place equally well at the inlet and/or at the outlet of the capillary.

According to a particular embodiment, the device, the subject matter of the invention, further comprises another vacuum enclosure, or second enclosure, provided to be at a second pressure, which may be below the first pressure, said second enclosure containing the third device and communicating with the first enclosure via a first orifice opposite the gravimetric detector.

The gravimetric detector may be selected from nanoelectromechanical systems, micro-electromechanical systems, quartz crystal microbalances, SAW (surface acoustic wave) resonators, BAW (bulk acoustic wave) resonators and impact detectors.

The first device may be selected from ultrasonic nebulizers, microwave induced nebulization devices, microcapillary array nebulizers and surface acoustic wave nebulizers.

BRIEF DESCRIPTION OF THE DRAWINGS

The present invention will be better understood on reading the description of embodiment examples given hereafter, purely as an indication and in no way limiting, and by referring to the appended drawings in which.

DETAILED DESCRIPTION OF PARTICULAR EMBODIMENTS

Figure 1:
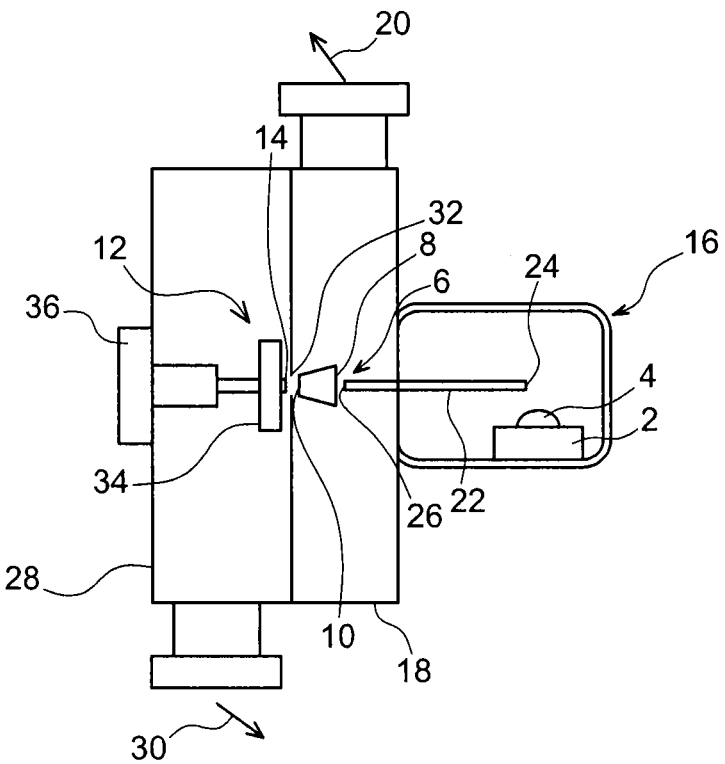
FIG. 1 is a schematic view of a particular embodiment of the device, the subject matter of the invention.

FIG. 1 is a schematic view of a particular embodiment of the device for determining the mass of a particle in suspension or in solution in a fluid, the subject matter of the invention. Said device comprises:
- a device 2 for the nebulization of the fluid, namely an analyte deposited in the form of droplet 4 in the example represented, to obtain a flux comprising at least the particle,
- a device for the guidance and the aerodynamic focusing of the flux, said device comprising an aerodynamic focusing lens 6 in which the inlet has the reference 8 and the outlet has the reference 10, and
- a device 12 for determining the mass of the particle by a frequency measurement, said third device comprising at least one gravimetric detector 14, arranged opposite the outlet 10 of the aerodynamic focusing lens 6, to receive the particle.

As may be seen, the device represented in FIG. 1 also comprises:
- a zone 16 at a given pressure, for example atmospheric pressure (around $10^5$ Pa), said zone containing the nebulization device 2, and
- a vacuum enclosure 18 that communicates with the zone 16 and contains the device 6 and in which a primary vacuum is established, namely a residual pressure of the order of $10^2$ Pa, using a primary pump which is symbolised by the arrow 20.

The device for the guidance and the aerodynamic focusing of the flux also comprises a capillary (rectilinear) 22 having an inlet orifice 24 in the zone 16 and an output orifice 26 in the enclosure 18, to place the zone 6 in communication with said enclosure 18. The inlet of the device for the guidance and the aerodynamic focusing of the flux is constituted of the inlet orifice 24 of the capillary 22 and the outlet of said device for the guidance and the aerodynamic focusing of the flux is constituted of the outlet 10 of the aerodynamic focusing lens 6.

It is pointed out that the capillary 22 also makes it possible to desolvate the particles in suspension or in solution.

The device represented in FIG. 1 also comprises another vacuum enclosure 28 in which a secondary vacuum is established, namely a residual pressure of the order of $10^{-2}$ Pa, by means of a turbomolecular pump which is symbolised by the arrow 30 (but, in other examples of the invention, the enclosures 18 and 28 could be at the same pressure).

The enclosure 28 contains the device 12 and communicates with the enclosure 18 via an orifice 32 opposite the detector 14.

Said detector 14 is mounted on a micro-positioning wafer 34, itself mounted on a sealed feed-through 36, as may be seen in FIG. 1.

The capillary 22 is aligned with said orifice 32, and the device 6 is comprised between the orifice 32 and the output orifice 26 of the capillary 22.

Thus, in the example of FIG. 1, the analytes are present in liquid phase and a portion of liquid is nebulized by the device 2, which produces an aerosol of very small droplets containing the analytes, mainly neutral, a part of which may potentially be ionized. Due to the pressure difference between the zone 16 and the enclosure 18, said aerosol is sucked into the input capillary 22. Opposite it is placed the aerodynamic focusing lens 6 which make it possible to guide equally well neutral species and ions to the detector 14, situated in the secondary vacuum enclosure 28.

The example of the invention, represented in FIG. 1, comprises two differential pumping chambers, namely the enclosures 18 and 28, but it is also possible to produce a device according to the invention comprising more than two differential pumping chambers, or even a single chamber.

In the example of FIG. 1, the detector 14 comprises a single NEMS but it is also possible to produce a device according to the invention where said detector comprises an array of such NEMS.

The means of reading and controlling the detector 14 are not represented. Said detector 14 may be temperature controlled, or not. The same is true of the inlet capillary 22.

It is advantageous to use a NEMS for the detection; but any other gravimetric detector (MEMS, QCM, SAW, BAW) may be used or, more generally, an inertial force detector, in particular an impact detector. With regard to the latter, reference may be made to the following document:

Jonghoo Park, Hua Qin, Mark Scalf, Ryan T. Hilger, Michael S. Westphall, Lloyd M. Smith and Robert H. Blick, 2011, "A Mechanical Nanomembrane Detector for Time-of-Flight Mass Spectrometry", *Nano Letters* 11: 3681-3684.

The aerodynamic focusing lens 6 is more simply known as "aerodynamic lens". It is known that the latter is in fact composed of a series of elementary aerodynamic lenses. Examples of aerodynamic lenses are given hereafter.

In the invention, the use of such lenses makes it possible to guide in particular neutral species in order to maximise measurement efficiency. Thus, an electrostatic guidance of the kind of that employed in ion optics is not used.

It is recalled that an aerodynamic lens comprises a series of orifices that constitute elementary aerodynamic lenses. Said orifices may have identical sizes (see FIG. 3, to which we will return hereafter) or different sizes, for example decreasing sizes (see FIG. 2, to which we will return hereafter). Through these orifices, a diluted aerosol is sucked up. The majority of the carrier gas (and the majority of the water molecules sucked up by the capillary 22 used in the example of FIG. 1), gas which is light and free of particles, diffuses in the volume that is located at the outlet of the lens, whereas the heavy particles (compared to molecules of gas), such as biological molecules, acquire a sufficient momentum to be collected, via the outlet flux, in the form of a very fine jet. Under certain conditions, said jet may even be focused into a point (focal point).

Aerodynamic lenses are commonly used in mass spectrometers intended to measure particles present in aerosols but, in the latter case, said lenses are not used for the guidance and the focusing of particles to a detector since the species are always ionized following their introduction in a mass spectrometer: they are used for the concentration and the sorting of species to be measured, before their passage in the spectrometer.

In an elaborated form, a focusing device that can be used in the invention comprises (see FIG. 2) an inlet orifice 38, enabling the control of the flux and the differential pressure, and an aerodynamic lens 40 constituted of a series of elementary lenses 41. Said series of elementary lenses 41 makes it possible to compress the flux lines of particles as they progress along the device. At the outlet of the series of elementary lenses 41, an orifice 42 may be placed, making it possible to capture the collimated beam of heavy particles, whereas the light molecules (for example solvent molecules) have volume diffusion and escape.

In this respect, reference may be made to the following document:

US 2008/0022853, "Aerodynamic lens particle separator", invention of P. Ariessohn.

Figure 3:
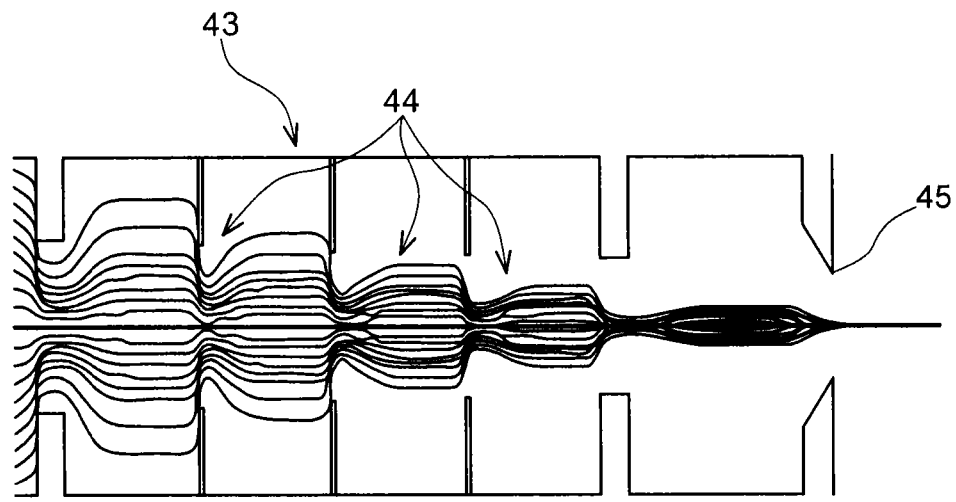
FIG. 3 illustrates schematically an example of a complete aerodynamic focusing system.

FIG. 3 illustrates schematically another example of aerodynamic focusing device, which may be used in the present invention and comprising an elementary aerodynamic lens or a series 43 of elementary aerodynamic lenses 44 and, at the outlet of said series of elementary lenses, a channel 45. Said channel 45 (or acceleration nose) may be a convergent channel or a convergent/divergent channel depending on the speed of the particles, and also helps the focusing of said particles It is pointed out that only a part of the components of the device of FIG. 3 may be used in the invention. With regard to said device represented in FIG. 3, reference may be made to the technical documentation supplied by the firm Aerodyne Research, and particularly:

ARI Aerosol Mass Spectrometer, Operation Manual, page 9.

Figure 2:
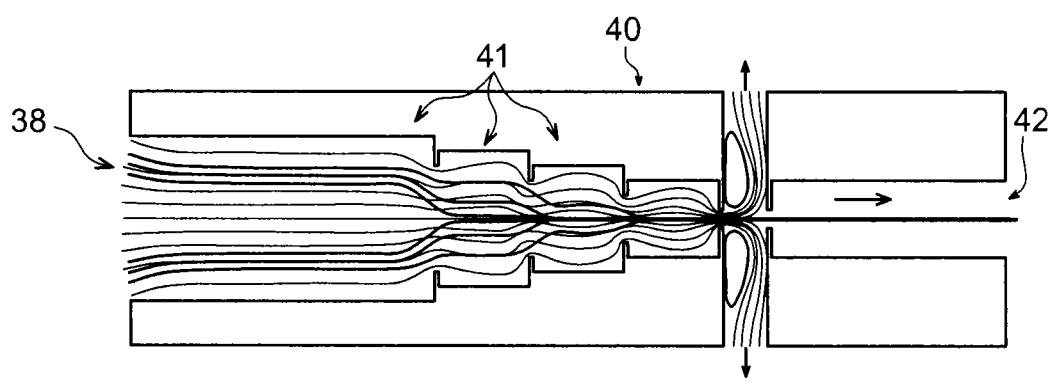
FIG. 2 illustrates schematically the principle of an aerodynamic focusing lens.

The aerodynamic lens 40 (respectively 43) of FIG. 2 (respectively FIG. 3) may obviously be associated with a capillary of the type of the capillary 22, placed at the inlet and/or at the outlet of said aerodynamic lens, or associated with an orifice of the type of the orifice 42 of FIG. 2.

Figure 4:
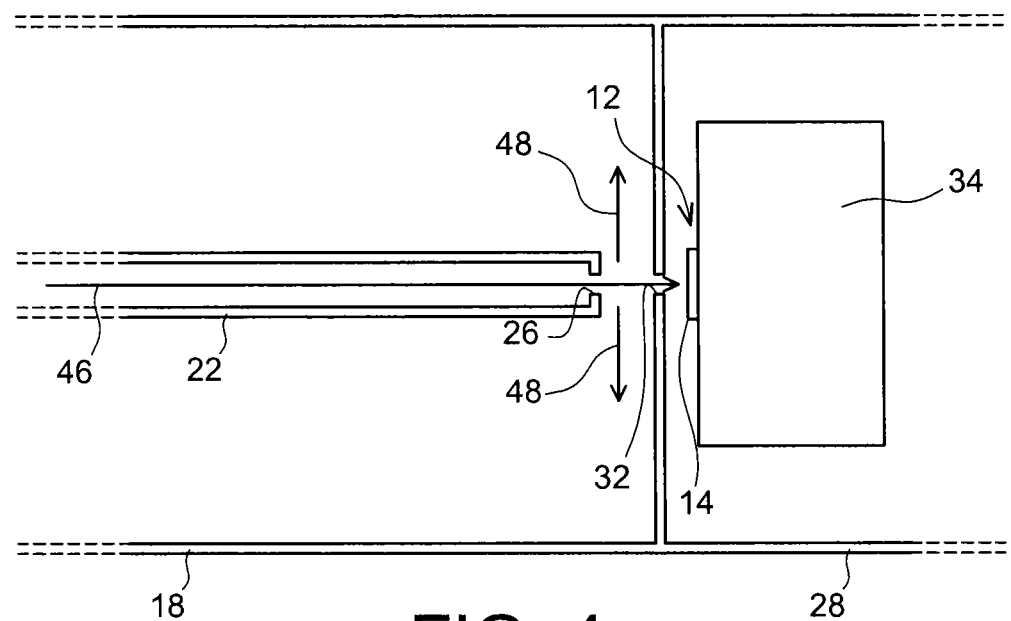
FIG. 4 illustrates schematically and partially a simpler example of aerodynamic focusing device, which may be used in the present invention.

FIG. 4 is a schematic and partial view of another device according to the invention, in which the aerodynamic focusing device is simply composed of the inlet capillary 22, of its output orifice 26 and of the inlet orifice 32 to the secondary vacuum enclosure 28 where the NEMS 14 is located. In this FIG. 4, the direction of circulation of the longitudinal fluxes is reversed compared to FIG. 1. And the arrows 48 represent a radial flux of light molecules at the outlet of the capillary 28.

In the invention, any type of nebulization device may be used, particularly an ultrasonic nebulizer, a microwave induced nebulization device or a microcapillary array nebulizer.

Advantageously, a SAWN is used, in other words a surface acoustic wave nebulizer. In this respect, reference may be made to the following document:

David R. Goodlett, Scott R. Heron and Jon Cooper, 2011, "Ions generated by surface acoustic wave device detected by mass spectrometry", WO 2011/060369 A1.

It involves, in this case, using a surface acoustic wave resonator, on which a drop of liquid containing the analytes is deposited. The surface acoustic wave produced by the resonator dissipates its energy in the liquid which, then, is nebulized.

This nebulization method has the interest of only ionizing a very small part of the analytes, also with a very low ionization energy. In addition, it is capable of desorbing entire drops of water, as well as biological particles in a wide range of masses. In addition, such a nebulization device is integrable. It may be obtained by collective micro-manufacturing methods. And, it may be envisaged to integrate the entire architecture of the present invention when such an integrable device is used.

In the examples of the invention given above, the guidance and focusing device is electrically neutral. This signifies that no electromagnetic field is applied to said device or produced by it.

For the guidance and the focusing, preferably such an electrically neutral device is used. Nevertheless, a guidance and focusing device that is not electrically neutral could also be used, more precisely in which the lateral face is polarised with a certain voltage in order to separate the neutral species from the ionized species or, conversely, to polarise the device so as to obtain an electromagnetic field capable of focusing only the neutral species.

In the example of FIG. 1, the aerodynamic lens 6 is associated with the capillary 22. But an embodiment of the invention may also be envisaged in which the second device, serving for the guidance and for the aerodynamic focusing of the flux, comprises a diaphragm or an orifice in place of the capillary.

The invention claimed is:

1. A device for determining the mass of at least one particle in suspension or in solution in a fluid, comprising:
a first nebulizing device configured to nebulize the fluid to obtain a flux comprising said at least one particle;
a second device configured for guiding and aerodynamic focusing of the flux, said second device comprising an inlet configured to receive the flux, and an outlet; and
a third device configured to determine a mass of said at least one particle by a frequency measurement, said third device comprising at least one gravimetric detector, arranged opposite to the outlet of the second device, configured to receive said at least one particle.

2. The device according to claim 1, wherein the second device is electrically neutral.

3. The device according to claim 1, wherein the second device comprises an aerodynamic lens.

4. The device according to claim 3, wherein the aerodynamic lens is associated, at the outlet, with an orifice.

5. The device according to claim 1, further comprising:
a zone at a given pressure containing the first nebulizing device; and
at least one first vacuum enclosure provided to be at a first pressure below a pressure of said zone, the first vacuum enclosure communicating with the zone and containing at least one part of the second device.

6. The device according to claim 5, wherein the second device further comprises a capillary having an inlet orifice in the zone and an output orifice in the first vacuum enclosure, to place the zone in communication with the first vacuum enclosure.

7. The device according to claim 6, wherein the second device further comprises an aerodynamic lens opposite the inlet orifice and/or output orifice of the capillary.

8. The device according to claim 5, further comprising a second vacuum enclosure provided to be at a second pressure, the second vacuum enclosure containing the third device and communicating with the first vacuum enclosure via a first orifice situated opposite the gravimetric detector.

9. The device according to claim 8, wherein the second pressure is lower than the first pressure.

10. The device according to claim 1, wherein the gravimetric detector is selected from nano-electromechanical systems, micro-electromechanical systems, quartz crystal microbalances, surface acoustic wave resonators, bulk acoustic wave resonators, and impact detectors.

11. The device according to claim 1, wherein the first nebulizing device is selected from ultrasonic nebulizers, microwave induced nebulization devices, microcapillary array nebulizers, and surface acoustic wave nebulizers.

* * * * *